United States Patent [19]

Volz

[11] 4,233,507
[45] Nov. 11, 1980

[54] COMPUTER TOMOGRAPHY TABLE CONTAINING CALIBRATION AND CORRELATION SAMPLES

[75] Inventor: Donald J. Volz, Mukwonago, Wis.

[73] Assignee: General Electric Company, Milwaukee, Wis.

[21] Appl. No.: 36,816

[22] Filed: May 7, 1979

[51] Int. Cl.³ .................... A61B 6/00; G12B 13/00
[52] U.S. Cl. ........................... 250/252; 250/445 T
[58] Field of Search ................. 250/252, 491, 445 T

[56] References Cited

U.S. PATENT DOCUMENTS

| | | | |
|---|---|---|---|
| 4,115,691 | 9/1978 | Oldendorf | 250/445 T |
| 4,124,799 | 11/1978 | Schittenhelm | 250/252 |

FOREIGN PATENT DOCUMENTS

| | | | |
|---|---|---|---|
| 402070 | 4/1974 | U.S.S.R. | 250/252 |
| 425146 | 9/1974 | U.S.S.R. | 250/252 |

*Primary Examiner*—Alfred E. Smith
*Assistant Examiner*—T. N. Grigsby
*Attorney, Agent, or Firm*—Douglas E. Stoner; Dana F. Bigelow

[57] ABSTRACT

A table top is positioned on a base for supporting a patient between a radiation source and a radiation detector of the computed tomography system. The table top has a supporting surface which is translatable in the longitudinal direction of the computed tomography system. The table top includes a plurality of samples of reference materials which extend uniformly and longitudinally along the underside of the supporting surface. The reference materials are stable and homogeneous throughout their length and have properties which correspond to known radiation attenuation coefficients. Each computed tomography slice will include a slice of each of the samples of reference material. The resulting image will display a cross sectional slice of each samples which can be used to calibrate the system or correlate the images of the patient. The table top may be equipped with a removable portion. The samples of reference materials can alternatively be longitudinally disposed within the removable portion above the supporting surface of the table top.

7 Claims, 5 Drawing Figures

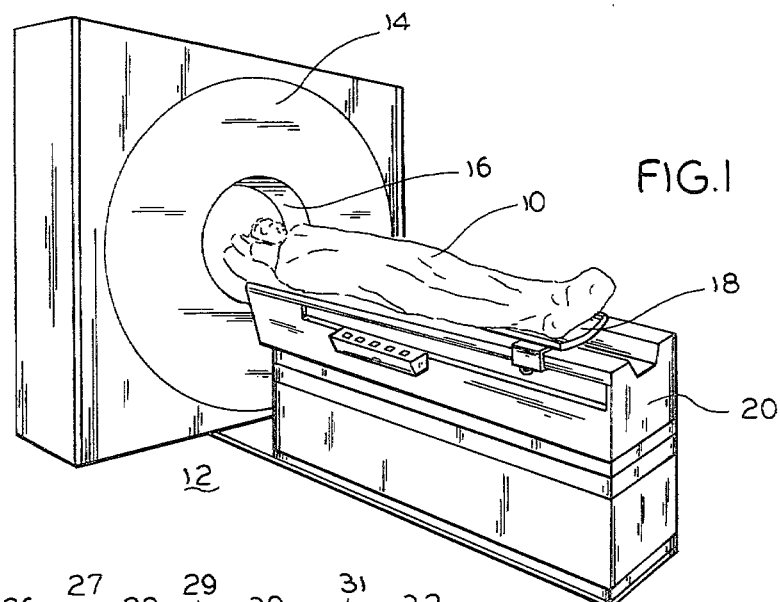
FIG.1
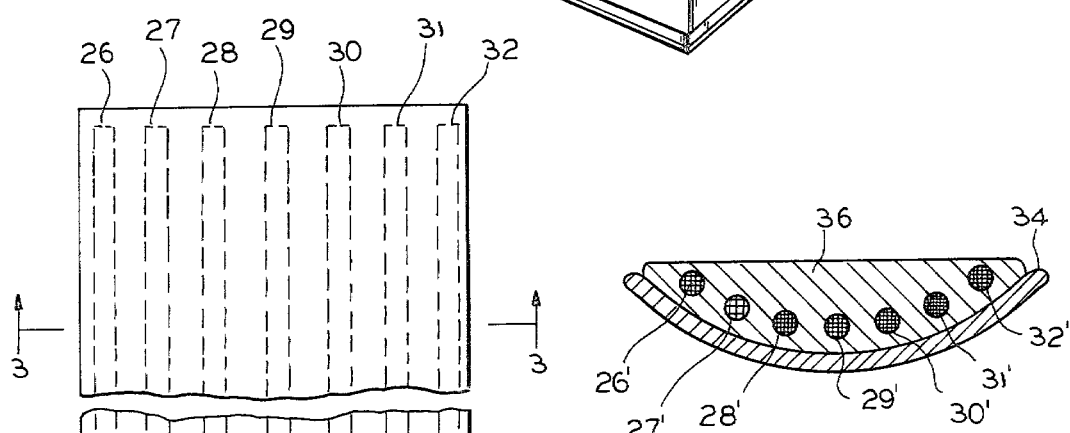
FIG.2
FIG.3A
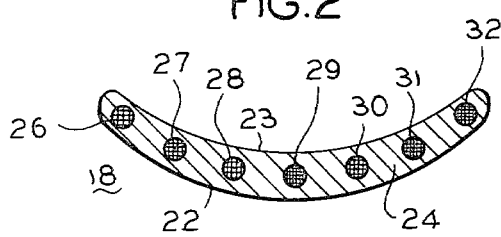
FIG.3
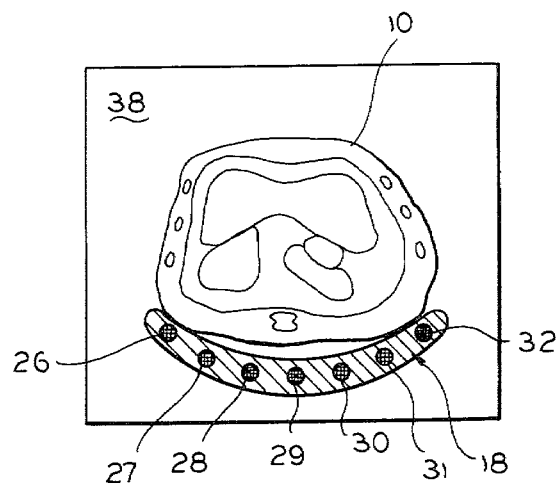
FIG.4

COMPUTER TOMOGRAPHY TABLE CONTAINING CALIBRATION AND CORRELATION SAMPLES

BACKGROUND OF THE INVENTION

The present invention relates to x-ray machine calibration devices and, specifically, to calibration devices for a computed tomography system.

In one method of computed tomography, a patient is supported for being translated along a longitudinal axis which coincides with the center of rotation of a rotatable gantry which has an x-ray source on one side of the center of rotation and an x-ray detector on the other side of the center of rotation. A fan-shaped x-ray beam that is thin in the longitudinal direction is projected through the patient as the gantry rotates so that the detector may develop signals indicative of x-ray transmission characteristics along a plurality of paths through the patient undergoing examination. Analog signals representative of x-ray attenuation by all of the volume elements in a layer of the patient at various rotational angles are then converted to digital signals which are used by a computer to produce signals that may thereafter be used to produce a reconstructed image of the layer. The reconstructed image of the radiation attenuation coefficients may be displayed in gray tones on the screen of a visual display.

One of the primary problems associated with computed tomography systems is proper calibration. The computed tomography system is quite complex and is subject to occasional interference and signal drift which may result in a slight shift in performance.

Another problem associated with system calibration is due to a phenomenon referred to as "beam hardening". The radiation attenuation coefficient is a property of every material and expresses the radiation absorption properties of the material at a specific x-ray energy. This attenuation coefficient is usually related to the attenuation coefficient of water and is referred to as a CT number expressed in "H-units". The CT numbers are relative and have reference points of −1000 for air and 0 for water with all other materials expressed as + or − a specific number of H units. Computed tomography radiation sources project polychromatic x-rays having energies which vary from 30 KeV to 120 KeV. The range of x-ray energies can produce a shift in CT numbers due to "hardening" of the ray spectrum as the x-rays penetrate the body. A shift in CT numbers can also be produced by repositioning the patient in a different location relative to the beam so that the patient is scanned by a different portion of the beam.

The attenuation coefficients and corresponding gray tones produced by the computed tomography system are relative and must be calibrated to known values. The system is usually calibrated on a regular basis by scanning a set of known reference samples mounted in what is referred to as a calibration phantom. Prior art phantoms are available in a number of variations, some being plastic replicas of the human body, or specific portions thereof, while others consist of actual human bones cast in plastics. Recent phantoms include a set of reference samples having known attenuation coefficients surrounded by a water medium housed within a plastic vessel. Phantoms used to calibrate computed tomography systems are usually cylindrical discs having a diameter ranging from 20 to 42 cm and having a thickness of approximately 10 cm. The phantoms are scanned in the same manner as the patient, and the resulting attenuation coefficients of the images of the system can be compared to the reference values of the phantom. Phantoms can also be used to correlate images from calibrated machines to analyze and interpret the images. A particular problem in utilizing conventional phantoms is that they cannot be used simultaneously with the analysis of a patient and that the calibration cannot be assured between applications of the phantom.

Accordingly, the object of the present invention is to provide a CT system with a set of reference samples having known radiation attenuation coefficients which appear in each reconstructed image from which to calibrate the system and to correlate the images of the patient.

SUMMARY OF THE INVENTION

The invention is directed to a table top which includes a sample of reference material which appears in each computed tomograph image and can be used to calibrate the system. The table top is positioned on a base for supporting a patient between a radiation source and a radiation detector of the computed tomography system. The table top has a supporting surface which is translatable in the longitudinal direction of the computed tomography system. The plurality of samples of reference materials extend uniformly and longitudinally along the underside of the supporting surface of the table. The reference materials are stable and homogeneous throughout their length and have properties which correspond to known radiation attenuation coefficients. Each computed tomography slice will include a slice of each of the samples of reference material. The resulting image will display a cross sectional slice of each sample which can be used to calibrate the system or correlate the images of the patient.

The table top may be equipped with a removable portion. The samples of reference materials can alternatively be longitudinally disposed within the removable portion above the supporting surface of the table top.

BRIEF DESCRIPTION OF THE DRAWINGS

While the novel features of the invention are set forth with particularity in the appended claims, the invention will be better understood, along with other features thereof, from the following detailed description taken in conjunction with the drawings in which:

FIG. 1 is a perspective view of a patient undergoing computed tomography analysis supported by the table top incorporating the present invention;

FIG. 2 is an enlarged, planned view of the table top shown in FIG. 1;

FIG. 3 is a sectional view taken along line 3—3 of FIG. 2;

FIG. 3A is a view similar to FIG. 3, showing another embodiment of the invention; and FIG. 4 is a view of the computed tomography image of the patient and table top shown in FIG. 1.

DESCRIPTION OF THE PREFERRED EMBODIMENT

Referring first to FIG. 1, there is shown a patient 10 in position for analysis on a computed tomography system 12. X-ray scanning and obtaining x-ray attenuation data on a multitude of small volume elements of the patient is carried out with components of a gantry which is generally designated by reference numeral 14. Gantry 14 is generally vertical having a cylindrical horizontal opening 16 for receiving the patient for examination. The details of the gantry are described in U.S. Pat. No. 4,093,860, entitled "Gantry for Computed Tomography" by Kelman, et al, and assigned to the same assignee as the present application. The details of the gantry are not shown, but generally include an x-ray source and collimator on one side of opening 16 which project a thin, fan-shaped beam of radiation which is received by an x-ray detector on the opposite side of the opening. A suitable detector is shown in U.S. Pat. No. 4,031,396 to Whetten, et al, and assigned to the assignee of this application. The patient 10 is supported in opening 16 by a table top 18, which is translatable in the longitudinal direction along a base 20. The discrete plurality of analog signals representative of x-ray attenuation by small volume elements in the patient are processed in a data acquisition system, after which the analog signals are converted to digital signals which are used by a computer to execute the image reconstruction algorithm. The above-described computed tomography system is generally known in the art.

Referring also to FIGS. 2 and 3, table top 18 can be described in greater detail. Present table tops are constructed with composite structure techniques which provide very high strength and very low x-ray absorption. An exemplary structure is composed of a Kelvar fiber and resin skin 22, forming a supporting surface 23 and enclosing an expanded foam inner core 24. The composite structure readily lends itself to the installation of a set of stable samples of reference materials, such as 26, 27, 28, 29, 30, 31, and 32. The samples of reference materials extend longitudinally along the table top adjacent the supporting surface 23. In this embodiment, the samples are enclosed within table top 18 under supporting surface 23.

The samples 26 through 32 are shown as cylindrical in shape and extend substantially along the entire length of table top 18. The samples have a diameter of approximately 5 cm and span approximately 1,000 pixels of the imaging system. However, smaller diameter samples are contemplated and the smallest possible samples should be used to minimize dose of the system. As one example of a set of samples of reference materials, various concentrations of dipotassium hydrogen phosphate solutions ($K_2HP_4$) could be used for samples having attenuation coefficients close to bone. Plastics of lower attenuation coefficients ($-25$ to $+25$ H units) could be used for samples corresponding to fat and muscle. It is not absolutely necessary that the samples correspond to the exact anatomy of a patient, but, more importantly, that the precise attenuation coefficients be known for each of the samples. An exemplary set of samples was suitably evaluated in which samples 26 through 22 had respective attenuation coefficients of 1,023, 258, 177, 37, 94, 508, and 908, as measured in H units. The higher number samples could be used to monitor bone deterioration. The foregoing samples were prepared by the various concentrations of $K_2HP_4$. Solid calibration samples are presently being developed by phantom manufacturing companies, such as RMI in Madison, Wisconsin, and ATS in South Norwalk, Connecticut. The solid calibration samples are composed of a variety of homogeneous synthetic or plastic materials.

Since each scan contains the reference materials, changes in body composition of the patient can be determined relative to the reference materials. Later scans can be analyzed independent of any drift in the performance of the system and independent of beam hardening effects provided the patient is scanned in the same position relative to the beam.

Referring to FIG. 3A, there is shown an alternative embodiment in which the samples of reference materials 26' through 32' are positioned above the supporting surface of a different table top 34. Table top 34 is composed of a composite structure, as similarly described in reference to table top 18. A removable portion 36 is positioned on the upper surface of table top 34. The set of samples of reference materials is longitudinally disposed above the table top 34 and enclosed within the removable portion 36. Other sandwiched-type embodiments varying in size and shape could be utilized; however, the significant factor is that the sample of reference material be longitudinally disposed so that it will be included in each slice of the computed tomography analysis. It is important that the samples be fixedly positioned in precisely the same location where mounted on the table top.

FIG. 4 illustrates a reconstructed computed tomography image 38, showing the cross section of the patient 10 and the table top 18. It is apparent that the set of samples of reference materials 26 through 32 will be shown in each computed tomography scan of the patient. Each image can be readily calibrated by comparison to the known reference materials, or the image of patient 10 can be better understood by correlation to the known attenuation coefficients shown by the sample of reference materials. Subsequent scans, with the same table top in the same position, are independent of system changes and beam hardening effects are minimized. Standard calibrated table tops could also be used to compare computed tomography images at different times, or even on entirely different systems and still provide a standard correlation for analysis.

While specific embodiments of the present invention have been illustrated and described herein, it is realized that modifications and changes will occur to those skilled in the art. It is, therefore, to be understood that the appended claims are intended to cover all such modifications and changes as fall within the true spirit and scope of the invention.

What is claimed is:

1. A table top positioned on a base for supporting a patient between a radiation source and a radiation detector of a computed tomography system, said table top comprising:
   a supporting surface which is translatable in the longitudinal direction of the tomography system, and
   at least one uniform sample of reference material disposed longitudinally within said table top, said reference material having properties which correspond to a known radiation attenuation coefficient.

2. The table top, as recited in claim 1, wherein said sample of reference material is longitudinally disposed on the underside of said supporting surface.

3. The table top, as recited in claim 1, which further comprises a removable portion which extends over said supporting surface wherein said sample of reference material is longitudinally disposed within said removable portion.

4. The table top, as recited in claim 1, wherein said sample of reference material comprises a homogeneous liquid solution.

5. The table top, as recited in claim 4, wherein said homogeneous liquid solution comprises a known concentration of dipotassium hydrogen phosphate.

6. The table top, as recited in claim 1, wherein said sample of reference material comprises a homogeneous synthetic or plastic material.

7. The table top, as recited in claim 1 which further comprises a plurality of said samples of reference materials.

* * * * *